United States Patent [19]

Leston

[11] 4,447,658

[45] May 8, 1984

[54] PROCESS FOR SEPARATING 3,5-XYLENOL OR 3,4-XYLENOL FROM OTHER POLYMETHYLATED PHENOLIC COMPOUNDS

[75] Inventor: Gerd Leston, Pittsburgh, Pa.

[73] Assignee: Koppers Company, Inc., Pittsburgh, Pa.

[21] Appl. No.: 431,651

[22] Filed: Sep. 30, 1982

[51] Int. Cl.³ .............................................. C07C 37/68
[52] U.S. Cl. .................................... 568/750; 568/751; 568/752
[58] Field of Search ........................ 568/750, 751, 752

[56] References Cited

U.S. PATENT DOCUMENTS

| | | | |
|---|---|---|---|
| 4,258,220 | 3/1981 | Leach | 568/752 |
| 4,267,389 | 5/1981 | Leston | 568/750 |
| 4,267,390 | 5/1981 | Leston | 568/750 |
| 4,267,391 | 5/1981 | Leston | 568/750 |
| 4,267,392 | 5/1981 | Leston | 568/750 |

OTHER PUBLICATIONS

Sharpless et al., "Jour. Organic Chemistry", vol. 40, No. 9, (1975), pp. 1252–1257.

*Primary Examiner*—Werren B. Lone
*Attorney, Agent, or Firm*—Daniel J. Long; Herbert J. Zeh, Jr.

[57] ABSTRACT

A process is disclosed for separating 3,5-xylenol or 3,4-xylenol from other closely boiling polymethylated phenolics by treating a mixture of the phenolics with a metal halide salt. The metal halide salt preferentially forms a complex with the xylenol over other related phenolics in the mixture. The preferentially-formed complex of the xylenol may then be isolated from the mixture and the complex decomposed to provide a product substantially enriched in, or substantially entirely composed of the xylenol.

12 Claims, No Drawings

PROCESS FOR SEPARATING 3,5-XYLENOL OR 3,4-XYLENOL FROM OTHER POLYMETHYLATED PHENOLIC COMPOUNDS

BACKGROUND OF THE INVENTION

1. Field of the Invention

Preferential complexation of one organic compound in a mixture of related compounds is a known technique for resolving mixtures of closely related compounds. Of particular interest herein are methods for isolating 3,5-xylenol and/or 3,4 xylenol from close boiling mixtures, by preferential complexation of one of the phenolics.

2. Description of the Prior Art

Mixtures of polymethyl phenolics are available as by-products from the coking of coal and the base extraction of petroleum fractions. The isolation and purification of individual phenolics is very difficult by the use of conventional separation methods such as fractional distillation and fractional crystallization. This fact may be seen from the table below which lists twelve phenols boiling within a 25° range.

| Phenol | Boiling Point (°C.) | Melting Point (°C.) |
| --- | --- | --- |
| 2,3-xylenol | 218 | 73 |
| 3,5-xylenol | 221 | 63 |
| 3,4-xylenol | 226 | 65 |
| 2,5-xylenol | 211 | 74 |
| 2,4-xylenol | 211 | 25 |
| 2,3,6-trimethylphenol | 220 | 62 |
| 2,4,6-trimethylphenol | 220 | 71 |
| 2,3,4-trimethylphenol | 237 | 81 |
| 2,3,5-trimethylphenol | 235 | 95 |
| 2,4,5-trimethylphenol | 236 | 72 |
| m-ethylphenol | 218 | −4 |
| p-ethylphenol | 219 | 46 |

There are chemical processes known for separating closely-related organic compounds by methods other than, or in addition to, energy-intensive physical separation techniques such as fractional distillation or fractional crystallization. These chemical processes involve a step of preferential complexation of one component of a mixture of closely-boiling compounds over other components of the mixture. For example, U.S. Pat. No. 4,267,389 to Leston, describes treating a phenolic mixture comprising para-cresol, methylated phenols and ethylated phenols with an inorganic halide salt, such as calcium bromide, to remove para-cresol from the mixture. Removal of para-cresol from the mixture involves formation of a complex between para-cresol and calcium bromide, which complex forms preferentially over complexes between calcium bromide and other components of the phenolic mixture.

Mixtures of various alcohols may be resolved by treatment with a halide salt. For example, in Sharpless et al., *J. Org. Chem.*, Vol. 40, No. 9, p.p. 1252–1257 (1975), there is reported a study of competition between pairs of mono-hydroxy alcohols and mono-hydroxy phenols for complex formation with a halide salt. This study finds that phenols as a class form poorer complexes than alcohols of comparable melting point, probably because the phenols are weaker bases than the comparable alcohols.

There remains need, therefore, for methods for resolution of mixtures of closely-related phenolics by chemical complexation methods, rather than by fractional crystallization or distillation.

SUMMARY OF THE INVENTION

A mixture of two or more polymethyl phenolics may be resolved into individual phenolic components by a process involving a step of forming a solid complex preferentially between a metal halide salt and one of the phenolics in the mixture containing at least one phenolic from the group consisting of 3,5-xylenol and 3,4-xylenol. A metal halide salt suitable for forming the solid complex may be selected from the group consisting of calcium bromide, calcium chloride, lithium bromide, magnesium chloride and magnesium bromide. Resolution of such a phenolic mixture may be accomplished by either of the following two preferred methods.

A first method involves bringing together a mixture of two or more phenolics at least one of which is 3,5-xylenol or 3,4-xylenol, and a selected metal halide salt, the metal halide being selected such that a complex forms with one of the above xylenols in preference to, or preferentially over, other phenolics in the mixture. This preferentially formed complex constitutes a solid material in contact with a liquid phase such as may be provided by aliphatic, alicyclic and aromatic hydrocarbons, and their chlorinated derivatives, ethers, esters and ketones. Also, any combination of such solvents may be used. Alcohols are specifically excluded as solvents inasmuch as they form complexes with the metal halide salt solvent. The solid complex may then be removed or isolated from the liquid phase and thereafter decomposed to a product comprising a predominantly greater amount of the preferentially-complexed phenolic than other phenolics, as compared to the relative amounts of phenolics present in the original mixture. The product may also contain phenolic derived from complexes which form with the selected metal halide salt, but in lesser amount than the amount of phenolic derived from the preferentially-formed complex.

A second method involves forming a mixture of two or more phenolics, at least one of which is either 3,5-xylenol or 3,4-xylenol, in contact with a selected metal halide salt, the metal halide salt initially present in an amount relative to one phenolic and selected such that one or more complexes form between the selected metal halide salt and one or more of the phenolics, but such that at least one of the phenolics forms no complex or forms a significantly lesser amount of complex with the selected metal halide salt than the preferentially-complexed phenolic. This phenolic which forms no complex, or which forms a complex in a significantly lesser amount than other phenolics, relative to amounts of phenolics originally present in the mixture, remains dissolved in the liquid phase. The solvent providing the liquid phase may then be removed or isolated from the preferentially-complexed phenolics which are present as solid material. Removal of the solvent provides a product containing an enriched amount of the phenolic which did not preferentially complex with the selected metal halide salt, as compared to the original mixture of phenolics.

One advantage provided by the process of the invention is good resolution or mutual separation of pairs of phenolics can be obtained from a mixture of two or more phenolics which separation would be substantially impossible to accomplish in a one-stage fractional distillation or crystallization. A second advantage resides in this chemical-separation process requiring significantly less energy to accomplish good resolution of the phenolics than physical-separation methods such as fractional distillation or crystallization.

The chemical-separation process of the invention may also be used advantageously in conjunction with conventional physical-separation processes. For example, calcium bromide complexation may be used in an initial treatment of a phenolic mixture for separating two or more compounds. Then, a resulting mixture of compounds having boiling points further apart can be treated by distillation or crystallization for more complete resolution of the mixture.

DETAILED DESCRIPTION OF THE INVENTION

The terms "phenol", "phenols", "phenolic" or "phenolics" as used herein includes xylenols; trimethylphenols and monoethylphenols. The phrases "resolving a mixture of phenolics" and "resolution of a mixture of phenolics" relate to a mechanism or a result in which the individual phenolic components of a mixture containing two or more phenolics may be separated or isolated from each other. Thus, the separation of a significant amount of one phenolic from a mixture of two phenolics constitutes a resolution of the mixture. The phrases also embrace separation of a multi-component mixture into groups of phenolics, each group containing two or more phenolics. Also included within the definition are treatments resulting in a significant increase in the amount of one or more phenolics as compared to the composition of the original mixture of phenolics, even where the original mixture contained relatively small amounts of the enriched phenolic. It is contemplated that a differentation or enrichment in the relative amounts of phenolics is a "significant enrichment" if treatment of a mixture provides an increase of at least about 20 weight percent in one or more of the phenolics as compared to the composition of the original mixture.

The phrases "preferentially-formed complex" and "predominantly-complexed phenolic" are intended as abbreviated descriptions of the complex comprising a selected metal halide salt and phenol which forms in an amount significantly greater than an amount of any other complex of another phenolic resulting from treatment of the phenolic mixture with the selected metal halide salt. Any complex formed will preferably be comprised substantially entirely of a complex of a single type of phenolic. It is recognized, however, that other phenolics in a starting mixture may form complexes with the selected salt in secondary or lesser amounts than the primary, predominantly-formed complex. Such secondary complex formation in lesser amounts is not deleterious provided that the ratio of the predominant complex to the secondary complex in the resulting solid material is sufficiently high to provide a useful resolution of a phenolic mixture. It is contemplated that a primary/secondary or predominant/lesser ratio of the relative amounts of complexes of the treated mixture constitutes a significant and usefully-resolved mixture of phenolics.

Mixtures of phenolics susceptible to treatment with the process of the invention include mixtures of two or more phenolics boiling in the range of about 210° C. to about 238° C. Such phenolics include 2,3-, 2,4-, 2,5-, 3,5- and 3,4-xylenols, 2,3,4-, 2,3,5-, 2,3,6-, 2,4,5- and 2,4,6-trimethylphenols and m,p-ethylphenols.

The family of metal halide salts which may be used in the process of the present invention is characterized by several common properties. For example, in addition to each member of the family being an inorganic salt of a metallic chloride or bromide, these halide salts are characterized in taking on water of hydration. The hydratable nature of these metal halide salts is believed to be significant in the mechanism of complex formation with the phenolics, even though no water is involved in the complexation reaction. Of the family of metal halide salts suitable for use in the invention, calcium bromide is preferred. It is also preferred, whether calcium bromide or calcium chloride or any other of the halide salts is used, that the salt have a water content, either as hydrate or occluded, of less than about ten weight percent. Also, it is preferred that the salt have a particle size less than about 200 mesh.

Solvents which may be used in the complexation reaction include those organic compounds which dissolve the phenolic mixtures but do not preferentially react with the metal halide salt. Solvents suitable include aliphatic, alicyclic and aromatic hydrocarbons, their chlorinated derivatives, ethers, esters and ketones. Alcohols are specifically excluded since they may form complexes with the metal halide salt. Mixtures of solvents may also be used.

The process of the invention is particularly suitable for resolving mixtures of closely boiling phenolics, one of which is 3,5- or 3,4-xylenol. Examples of such mixtures include the following: 3,5-xylenol and 2,3,6-trimethylphenol; 3,5-xylenol and 2,4,6-trimethylphenol; 3,5-xylenol and 2,3-xylenol; 3,4-xylenol and 2,3,6-trimethylphenol; 3,4-xylenol and 2,4,6-trimethylphenol; 3,4-xylenol and 2,3-xylenol and mixtures consisting of three of these five above mentioned components, at least one of which is 3,5-xylenol of 3,4-xylenol. Generally, in a mixture containing 3,5-xylenol, the 3,5-xylenol is preferentially complexed. Generally, in a mixture containing 3,4-xylenol, the 3,4-xylenol is preferentially complexed with calcium bromide.

Generally, the metal halide salt is added to the mixture of phenolics dissolved in, or in contact with, a solvent. For calcium bromide, for example, the salt is preferably added in amount in a range from about 0.1 mole to about 4 moles to one mole of the phenolic to be preferentially complexed. Usually, the complexation reaction takes place in the presence of a catalyst such as a lower aliphatic alcohol. A typical catalytic amount of the alcohol would be approximately five mole percent of the alcohol based on the total phenolic content.

After the aforementioned components are brought together as a mixture, usually in the form of a slurry, the mixture is agitated for a period of time sufficient for the phenolic-metal halide salt complex to form. A typical mixing time is in a range from about one hour to about 24 hours. Mixing is typically conducted at room temperature and at atmospheric pressure, although the complexation reaction may be conducted at practically any temperature in a range from about 0° C. to about 150° C. Superatmospheric pressure may be used to avoid escape of reactants and solvents. Also, care must be taken to exclude ambient moisture from the reaction mixture.

After the mixing period, the mixture contains a fluffy, white or gray solid material component in contact with a liquid component. The solid material may be separated from the liquid component by any conventional separation techniques such as by decanting, by centrifugation, or by filtration. If filtration is used to separate the solid material from the liquid, the filtration may be conducted with the aid of pressure gradient applied across the filter medium. The separated solid material may be washed with small portions of solvent, and the washings thereafter may be combined with the filtrate. After the washing step, the separated solid material may be optionally dried, usually by means of low heat or in a desiccator under reduced pressure. The drying step is carried out until the solid material reaches a constant weight.

The solid material, which contains the phenolic-metal halide salt complex, is then decomposed to provide the desired phenolic. Decomposition may be accomplished by hydrolysis of the complex in water, by heating of the complex at a temperature usually in a range of from about 150° C. to about 350° C., or by treatment with an alcohol, such as a lower boiling aliphatic alcohol. Preferred decomposition methods include water hydrolysis and heat treatment of the complex. In decomposition of the complex by water hydrolysis, the phenolic may be recovered by treating the water with an organic solvent, typically ether. In decomposition of the complex with heat, the phenolic may be separated by filtration, centrifugation or distillation from the metal halide salt residue. In either of these decomposition methods, the metal halide salt may be recovered and recycled for treatment of another mixture of phenolics, or for subsequent treatment of the separated phenolics in the event of incomplete separation of the mixture of phenolics.

It is an important feature of the invention that the liquid portion of the mixture treated with the metal halide salt contains the phenolic which less predominantly forms a complex with the metal halide salt or which forms substantially no complex with the metal halide salt. Thus the liquid portion of the treated mixture will be enriched in this phenolic and depleted in the phenolic which predominantly complexes with the metal halide salt. This phenolic may be recovered from this liquid portion by conventional distillation or fractionation techniques.

In order to demonstrate the invention, a series of individual polymethylated phenolics were treated with calcium bromide to show the formation of a phenolic-$CaBr_2$ complex, as described in Example I to IX.

EXAMPLE I

A reaction vessel equipped with stirring means was charged with 3.05 g 3,5-xylenol (25 mmole), 0.1 ml absolute ethanol and 25 ml hexane as a solvent for the organic components. To the reaction vessel was added 5.0 g powdered anhydrous calcium bromide (25 mmole) to form a slurry-like mixture. The reaction vessel was equipped with a drying tube filled with a desiccant, such as anhydrous calcium sulfate, for the purpose of excluding atmospheric moisture from the reaction mixture during the reaction period. A complexation reaction was run by stirring this mixture for about 1.5 hours at room temperature, after which time 10 ml hexane was added. Thereafter, the mixture was stirred about 5 minutes. The mixture was observed to contain a large amount of fluffy, white solid material suspended in the liquid solution. The mixture was filtered under suction, in a manner to minimize exposure of the mixture to ambient moisture, so as to separate the fluffy solid material from the liquid component. The separated solid material was washed with small portions of hexane and the hexane washings were combined with the filtrate. The washed solid material was dried in a desiccator under a pressure of 1 mm Hg absolute for a period of time until a substantially constant weight was recorded of 7.30 g. Inasmuch as the dried solid material weighed 7.30 g, it was determined that 2.30 g 3,5-xylenol had complexed with the calcium bromide.

EXAMPLE II

A complexation reaction was run generally was described in Example I with a mixture of 12.2 g 3,5-xylenol (100 mmole), 0.1 ml absolute ethanol, and 5.0 g powdered anhydrous calcium bromide (25 mmole) in some toluene. After the mixture was stirred for a total of 18 hours it was worked up. A washed-and-dried solid material was obtained in an amount of 8.75 g. The filtrate was concentrated on a steam bath to a constant weight of 8.2 g. Inasmuch as 3.75 g 3,5-xylenol apparently complexed with 5.0 g $CaBr_2$, it was determined that the 3,5-xylenol/$CaBr_2$ molar ratio was 1.2:1.0.

EXAMPLE III

A complexation reaction was run generally as described in Example I with a mixture of 6.1 g 3,4-xylenol (50 mmole), 0.1 ml absolute ethanol, 10.0 g powdered anhydrous calcium bromide (50 mmole) and 25 ml of toluene. After the mixture was stirred for a total of 18 hours it was diluted with toluene. A washed-and-dried solid material was obtained in an amount of 14.9 g. The filtrate was concentrated on a steam bath to a constant weight of 12.75 g. Inasmuch as 4.9 g 3,4-xylenol had apparently complexed with 5.0 g $CaBr_2$, it was determined that the 3,4-xylenol/$CaBr_2$ molar ratio was 0.61:1.0 in this complex.

EXAMPLE IV

A complexation reaction was run as generally described in Example III with a starting mixture of 12.2 g 3,4-xylenol (100 mmole), 0.1 ml absolute ethanol, 5.0 g powdered anhydrous calcium bromide (25 mmole) and some of toluene. After the mixture was stirred for a total of 18 hours it was worked up. A washed-and-dried solid material was obtained in an amount of 10.7 g for a 3,4-xylenol/$CaBr_2$ molar ratio of 1.9:1.0.

EXAMPLE V

A complexation reaction was run as generally described in Examples I and IV with a mixture of 12.2 g 3,4-xylenol (100 mmole), 0.1 ml absolute ethanol, 10.0 g powdered anhydrous calcium bromide (50 mmole) and 50 ml of toluene. After the mixture was stirred for a total of 48 hours it was worked up. A washed-and-dried solid material was obtained in an amount of 20.75 g. The filtrate left 3.9 g after removal of the solvent. Inasmuch as 10.75 g 3,4-xylenol had apparently complexed with 10.0 g $CaBr_2$, it was determined that the 3,4-xylenol/$CaBr_2$ molar ratio was 1.8:1.0.

EXAMPLE VI

A complexation reaction was run as generally described in Example I with a mixture of 12.2 g 2,4-xylenol (100 mmole) and 20.0 g powdered anhydrous calcium bromide (100 mmole) in some of hexane. After the mixture was stirred for five hours no complex seemed to have formed because the solid settled rapidly when stirring was stopped. Next, 0.1 ml of ethanol was added and stirring was resumed. After 1.25 hours, the mixture became thick and it was diluted with 50 ml hexane. Twice more 50 ml of hexane had to be added. A washed-and-dried solid material was obtained in an amount of 7.29 g. The filtrate was concentrated on a steam bath to a constant weight of 12.75 g. Inasmuch as 2.3 g o-t-butylphenol apparently complexed with 5.0 g $CaBr_2$, it was determined that the 2,4-xylenol/$CaBr_2$ molar ratio was 0.61:1.0.

EXAMPLE VII

A mixture of 12.2 g (100 mmole) of 2,4-xylenol (Aldrich, 99%), 5.0 g (25 mmole) calcium bromide, five drops of ethanol and 30 ml of toluene was stirred magnetically for several hours but no complex formed. A small amount of previously prepared calcium bromide/2,4-xylenol complex was added and stirring was continued overnight. The thick purple complex was diluted with solvent and filtered yielding 5.5 g of fine product and 0.35 g of coarse product on drying. Assuming the coarse material to be unreacted calcium bromide, the phenol/salt molar ratio is 0.30; assuming it to be complex, the ratio is 0.28. The 2,4-xylenol recovered from the filtrate amounted to 10.9 g.

EXAMPLE VIII

A solution of 12.2 g (100 mmoles) of 2,5-xylenol and ten drops of ethanol in 100 ml of toluene was stirred magnetically for 16 hours with 5.0 g (25 mmoles) of calcium bromide which had been reacted with m-cresol and the m-cresol complex decomposed by heating to 200° under reduced pressure. The solid amounted to 6.85 g corresponding to a 2,5-xylenol/calcium bromide molar ratio of 0.61. The filtrate left 10.3 g after base extraction, acidification, crystallization, filtration and drying.

EXAMPLE IX

A solution of 6.1 g (50 mmoles) of 2,3-xylenol and ten drops of ethanol in 60 ml of toluene was stirred with 2.5 g (12.5 mmoles) of "m-cresol-activated calcium bromide" for 22 hours. The m-cresol-activated $CaBr_2$ was prepared as described in Example VIII. The solid was worked up and amounted to 3.45 g. The filtrate, on extraction with caustic, acidification, filtration and drying, gave 5.0 g. Thus the molar ratio of 2,3-xylenol to calcium bromide was 0.62. The presence of 2,3-xylenol in the solid was further verified by GC analysis of the organic extract of the hydrolyzed solid.

As shown in Examples X to XVII, various synthetic mixtures of phenolics, containing 3,5-xylenol or 3,4-xylenol were prepared for treatment with calcium bromide to show the preferential complexation of one of the above phenolic over another phenolic, so as to allow separation of two or more phenolics. In the working examples which follow, the extracted-and-decomposed complexes of the separated solid material and the liquid portions were subjected to GC or IR analysis to determine the relative amounts of the phenolics in the solid material and in the liquid filtrate.

EXAMPLE X

A solution containing 6.10 g (50.0 mmoles) of 3,5-xylenol, 6.10 g of 2,3,6-trimethylphenol (95%) pure, and 0.1 ml ethanol in 50 ml of benzene was stirred magnetically at room temperature with 10.00 g (50.0 mmoles) of dry, powdered $CaBr_2$. After three hours the mixture had become thick and 100 ml of benzene was added. After the weekend, the mixture was again thick and stirring had stopped. Stirring was restarted for 15 minutes and then the solid was filtered by suction, washed with benzene and dried in vacuo to a constant weight of 12.96 g. A sample of the solid was decomposed by water-acetone mixture and by methanol and analyzed by GC. Also analyzed were the original solution and the combined filtrate and washings with the following results (in area %):

| Sample | 3,5-Xylenol | 2,3,6-trimethlyphenol | Unknown |
|---|---|---|---|
| Feed | 49.3, 49.2 | 48.0, 48.0 | 1.5, 1.5 |
| Complex | 95.5,[1] 98.5[2] | 2.0,[1] 1.3[2] | — |
| Filtrate | 33.6 | 63.0 | 2.7 |

[1]Decomposed by methanol.
[2]Decomposed by water-acetone.

EXAMPLE XI

A solution of 6.1 g (50.0 mmoles) of 3,4-xylenol, 6.1 g, 2,3,6-trimethylphenol (95% pure) and 0.1 ml ethanol in 150 ml of benezene was magnetically stirred with 10.00 g (50.0 mmoles) of dry, powdered $CaBr_2$. The stirring had stopped during the weekend and the solid was filtered by suction, washed with benzene and dried in vacuo to a constant weight of 12.79 g. A sample of the solid was hydrolyzed in acetone-water and analyzed by GC as were the feed and the combined filtrate and washings with the following results (in area %):

| Sample | 3,4-Xylenol | 2,3,6-Trimethylphenol |
|---|---|---|
| Feed | 41.7, 8.4 | 48.3, 50.6 |
| Complex | 97.7, 97.1 | 2.3,[1] 2.9[1] |
| Filtrate | 30.9 | 63.3 |

[1]includes impurities, possibly 2,3-xylenol.

EXAMPLE XII

A solution of 3.05 g (50 mmoles) of 3,5-xylenol, 3.05 g 2,4,6-trimethylphenol and 0.1 ml ethanol in 50 ml of benzene was stirred magnetically with 5.00 g (25 mmoles) of dry powdered $CaBr_2$ in the absence of moisture (drying tube). After 1.5 hours, another 40 ml of benzene was added. The mixture was too viscous to stir the following morning. The solid was filtered by suction, washed with benzene and dried to a constant weight of 5.39 g. A sample of the solid was decomposed in methanol and analyzed by GC. Also analyzed were the resulting solution and the combined filtrate and washings. The analytical results were as follows (in area %):

| Sample | 3,5-Xylenol | 2,4,6-Trimethylphenol |
|---|---|---|
| Feed | 49.0, 49.0 | 51.0, 50.8 |
| Solid | 85.5, 85.8 | 14.5, 14.2 |
| Filtrate | 45.5, 45.5 | 54.5, 54.5 |

EXAMPLE XIII

A solution of 3.05 g (50 mmoles) of 3,4-xylenol, 3.05 g of 2,4,6-trimethylphenol and 0.1 ml of ethanol in 50 ml of benzene was stirred magnetically with 5.00 g (25 mmoles) of dry, powdered $CaBr_2$ in the absence of moisture (drying tube). Two increments of 40 ml each of benzene were added during the first two hours to keep the mixture stirring. The following morning, the mixture was a gel and stirring had stopped. The solid was filtered by suction, washed with benzene and dried in vacuo to a constant weight of 5.75 g. A sample of the solid was decomposed in methanol and analyzed by GC. Samples of the feed and combined filtrate and washings were also analyzed with the following results (in area %):

| Sample | 3,5-Xylenol | 2,4,6-Trimethylphenol |
|---|---|---|
| Feed | 49.5, 44.1 | 50.0, 55.5 |
| Complex | 98.2 | 0.6 |
| Filtrate | 37.5, 34.2 | 62.0, 65.4 |

EXAMPLE XIV

A solution of each 3.05 (25.0 mmoles) of 3,5-xylenol, 2,3-xylenol and 0.1 ml ethanol in 100 ml of toluene was stirred magnetically with 5.00 g (25.0 mmoles) of dry, powdered $CaBr_2$ in the absence of moisture (drying tube). The following morning the solid was filtered by suction, washed with toluene and dried in vacuo to a constant weight of 5.17 g. A sample of the solid was decomposed in methanol and analyzed by GC. Samples of the original solution and the combined filtrate and washings were also analyzed with the following results (in area %):

| Sample | 3,5-Xylenol | 2,3-Xylenol |
|---|---|---|
| Feed | 48.4 | 51.6 |
| Complex | ca. 99 | trace |
| Filtrate | 43.6, 40.6 | 56.4, 59.4 |

A sample of the solid was hydrolyzed in water and the mixture was extracted twice with $CS_2$. IR of the extracts showed 3,5-xylenol with a trace of 2,3-isomer.

EXAMPLE XV

A solution of each 3.05 g (25.0 mmoles) of 3,4-xylenol and 2,3-xylenol and 0.1 ml of ethanol in 100 ml of toluene was stirred magnetically with 5.00 g (25.0 mmoles) of dry powdered $CaBr_2$ in the absence of moisture (drying tube). The following morning the stirring had stopped because the mixture had become thick. The solid was filtered by suction, washed with toluene and dried in vacuo to a constant weight of 6.45 g. A sample of the solid was decomposed in methanol and analyzed by GC. Samples of the original solution and the combined filtrate and washings were also analyzed with the following results (in area %):

| Sample | 2,3-Xylenol | 3,4-Xylenol |
|---|---|---|
| Feed | 52 | 48 |
| Complex | 9 | 91 |
| Filtrate | 65 | 35 |

EXAMPLE XVI

A solution of 1.50 g of each 3,5-xylenol, 2,3-xylenol, 2,3,6-trimethylphenol and 2,4,6-trimethylphenol and 0.1 ml ethanol in 50 ml of toluene was stirred magnetically with 5.00 g of dry, powdered $CaBr_2$ in the absence of moisture (drying tube). On the following morning, the solid was filtered by suction, washed with toluene and dried in vacuo to a constant weight of 5.10 g. A sample of the solid was decomposed in methanol and analyzed by GC. Samples of the original solution and the combined filtrate and washings were also analyzed by GC with the following results (in area %):

| Sample | Xylenols | | Trimethylphenols | |
|---|---|---|---|---|
| | 3,5- | 2,3- | 2,4,6- | 2,3,6- |
| Feed | 22 | 27 | 24 | 27 |
| Complex | 100 | 0 | 0 | 0 |
| Filtrate | 21 | 28 | 24 | 27 |

A sample of the solid was hydrolyzed in water and the mixture was extracted twice with $CS_2$. The phenolic component of the extract was identified as 3,5-xylenol by IR.

EXAMPLE XVII

A solution of 1.50 g of each 3,4-xylenol, 2,3-xylenol, 2,3,6-trimethylphenol and 2,4,5-trimethylphenol and 0.1 ml ethanol in 50 ml of toluene was stirred magnetically with 5.00 g of dry powdered $CaBr_2$ in the absence of moisture (drying tube). The following morning the mixture was very thick and barely stirring. The solid was filtered by suction, washed with toluene and dried in vacuo to a constant weight of 5.56 g. A sample of the solid was decomposed in methanol and analyzed by GC. Samples of the original solution and the combined filtrate and washings were also analyzed by GC with the following results (in area %)[1]:

| Sample | Xylenol | | Trimethylphenol | |
|---|---|---|---|---|
| | 2,3- | 3,4- | 2,4,6- | 2,3,6- |
| Feed | 25.0 | 20.8 | 28.7 | 25.4 |
| Complex | 3.8 | 92.1 | 0 | 4.1 |
| Filtrate | 26.8 | 14.5 | 31.2 | 27.6 |

[1] All are averages of two determinations.

EXAMPLE XVIII

A sample of tar acid gave the following GC analyses:

| Component | Area Percent |
|---|---|
| o-Cresol | 0.03 |
| m,p-Cresol | 1.08 |
| 2,4–2,5-Xylenol | 14.74 |
| 3,5-Xylenol | 72.20 |
| 3,4-Xylenol group | — |
| 2,3,5-Trimethylphenol | 11.95 |

A solution of this tar acid, 17.5 g (corresponding to 0.10 mmole of 3,5-xylenol at 70% concentration), in 50 ml of hexane and 20.0 g of anhydrous ball-milled calcium bromide (0.10 mmole) were magnetically stirred in a 250 ml Erlenmeyer flask equipped with a drying tube. It solidified after 6-8 hours. On the following day, 100 ml of hexane was added and stirring was resumed for four hours. The product was filtered and the residue was washed with solvent. It was dried in vacuum and left 24.60 g. The filtrate was evaporated to constate weight on a steam bath and yielded 12.95 g. GC analyses of a hydrolyzed sample of the solid and the original filtrate gave the following results:

| Component | Solid (hydrolyzed) | Filtrate |
|---|---|---|
| m,p-Cresol | .69, 0.73 | 1.10 |
| 2,4–2,5-Xylenol | 1.91, 2.03 | 21.79 |
| 3,5-Xylenol | 97.39, 96.33 | 59.79 with shoulder |
| 3,4-Xylenol group | — | 13.73 |

| Component | Solid (hydrolyzed) | Filtrate |
|---|---|---|
| trimethylphenol | — | 4.03 |

What is claimed is:

1. A process for resolving a mixture of two or more polymethylated phenolics at least one of which is selected from the group consisting of 3,5-xylenol and 3,4-xylenol, comprising the step of treating a mixture of two or more closely-boiling polymethylated phenolics at least one of which is selected from the group consisting of 3,5-xylenol and 3,4-xylenol with a metal halide salt selected from the group consisting of calcium bromide, calcium chloride lithium bromide, magnesium chloride and magnesium bromide, at a temperature of from about 0° C. to about 150° C., so as to form preferentially a complex comprised of the selected metal halide salt and one of the phenolics, whereby the preferentially-formed metal halide salt-phenolic complex may be isolated and thereafter decomposed to a product comprising a predominantly greater amount of one phenolic over other phenolics present, as compared to the relative amounts of phenolics present in the original mixture of phenolics.

2. The process of claim 1 wherein the polymethylated phenolics of the mixture are selected from the group consisting of dimethylphenol, trimethylphenol, 3,5-xylenol and 3,4-xylenol.

3. The process of claim 1 wherein one of the polymethylated phenolics in the mixture is 3,5-xylenol and another of the polymethylated phenolics in the mixture is selected from the group consisting of dimethylphenol and trimethylphenol.

4. The process of claim 1 wherein of the polymethylated phenolics in the mixture is 3,4-xylenol and another of the polymethylated phenolics in the mixture is selected from the group consisting of dimethylphenol and trimethylphenol.

5. The process of claim 1 wherein said selected metal halide salt is calcium bromide.

6. A process for resolving a mixture of two or more phenolics at least one of which is selected from the group consisting of 3,5-xylenol and 3,4-xylenol phenolic, comprising the step of forming a mixture of two or more phenolics in a liquid phase, at least one of which phenolics is selected from the group consisting of 3,5-xylenol and 3,4-xylenol, and a metal halide salt selected from the group consisting of calcium bromide, calcium chloride, lithium bromide, magnesium chloride and magnesium bromide, said mixture having a temperature of from about 0° C. to about 150° C., in relative amounts sufficient to form an insoluble complex between the selected metal halide salt and one of said xylenols, but such that at least one other of the phenolics either forms no complex with the selected metal halide or forms a complex in a relative amount which is significantly less than the amount of the complex formed with xylenols, said other phenolic remaining in the liquid phase;

whereby phenolic product may be recovered from the liquid phase, the product comprising a predominantly greater amount of said other phenolic than was present in the original liquid phase.

7. The process of claim 6 wherein one of said phenolics is 3,5-xylenol which forms a complex with calcium bromide and wherein said other phenolic is a close boiling homolog of 3,5-xylenol which remains in the liquid phase in a predominantly greater amount was present.

8. The process of claim 6 wherein one of said phenolics is 3,4-xylenol which forms a complex with calcium bromide and wherein said other phenolic is a close boiling homolog of 3,4-xylenol which remains in the liquid phase in a predominantly greater amount than was present in the original liquid phase.

9. A process for resolving a phenolic mixture containing 3,5-xylenol and another phenolic selected from the group consisting of dimethylphenol and trimethylphenol, the process comprising the steps of (a) bringing together for from about one hour to about 24 hours calcium bromide and a mixture of phenolics containing 3,5-xylenol and another phenolic selected from the group consisting of dimethylphenols and trimethylphenols at a temperature of from about 0° C. to about 150° C. in amounts sufficient to form an insoluble solid material in contact with a liquid, the phenolic contained in the solid material being predominantly or substantially entirely 3,5-xylenol present as a calcium bromide-3,5-xylenol complex; and (b) separating the insoluble solid material form the liquid and thereafter treating the material to decompose the complex, whereby a phenolic product is obtained comprising predominantly or substantially entirely 3,5-xylenol.

10. The process of claim 9 wherein the molar ratio of 3,5-xylenol:calcium bromide in the starting mixture is in a range from about 0.2:1.0 to about 5:0:1.1.

11. A process for resolving a phenolic mixture containing 3,4-xylenol and another phenolic selected from the group consisting of dimethylphenol and trimethylphenol, the process comprising the steps of (a) bringing together for from about one hour to about 24 hours calcium bromide and a mixture of phenolics containing 3,4-xylenol and another phenolic selected from the group consisting of dimethylphenols and trimethylphenols at a temperature of from about 0° C. to about 150° C. in amounts sufficient to form an insoluble solid material in contact with a liquid, the phenolic contained in the solid material being predominantly or substantially entirely 3,4-xylenol present as a calcium bromide-3,4-xylenol complex; and (b) separating the insoluble solid material form the liquid and thereafter treating the material to decompose the complex, whereby a phenolic product is obtained comprising predominantly or substantially entirely 3,4-xylenol.

12. The process of claim 11 wherein the molar ratio of 3,4-xylenol:calcium bromide in the starting mixture is in a range from about 0.2:1.0 to about 5.0:1.0.

* * * * *